Figure 1:
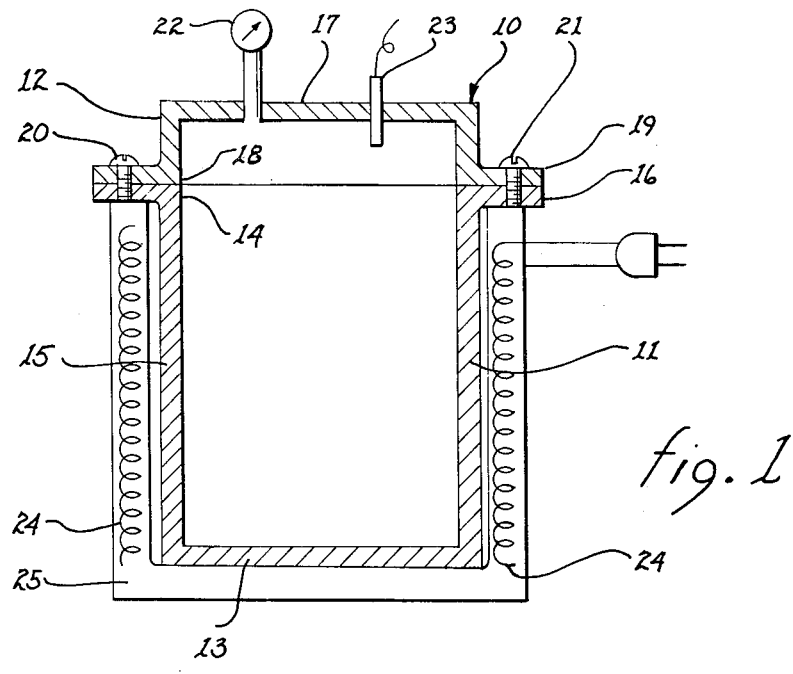

United States Patent [19]

Akcasu

[11] 4,070,289

[45] Jan. 24, 1978

[54] PREPARATION OF PYROGEN-FREE WATER

[76] Inventor: Alaeddin Akcasu, Dept. of Pharmacology, University of Istanbul, Istanbul, Turkey

[21] Appl. No.: 660,095

[22] Filed: Feb. 23, 1976

[51] Int. Cl.$^2$ .......................... B01D 35/18; C02B 1/02
[52] U.S. Cl. .......................... 210/71; 21/93; 165/2; 165/132; 165/144; 165/157; 210/175
[58] Field of Search .......................... 210/71, 175; 21/93, 21/94, 95; 203/11, 12, DIG. 11; 165/1, 2, 132, 144, 157

[56] References Cited

U.S. PATENT DOCUMENTS

| | | | |
|---|---|---|---|
| 1,819,618 | 8/1931 | Munters | 21/94 |
| 2,357,634 | 9/1944 | Crites | 99/330 |
| 2,648,018 | 8/1953 | Meier | 21/95 |
| 3,215,275 | 11/1965 | Bastecky et al. | 210/71 |
| 3,254,943 | 6/1966 | Palm | 21/94 |
| 3,276,458 | 10/1966 | Iversen et al. | 210/167 |
| 3,410,650 | 11/1968 | Bramson | 21/94 |
| 3,558,437 | 1/1971 | Metzger et al. | 203/11 |
| 3,579,290 | 5/1971 | Pickstone | 21/93 |
| 3,681,008 | 8/1972 | Black | 21/93 |
| 3,809,858 | 5/1974 | Boggs | 99/330 |

*Primary Examiner*—Frank W. Lutter
*Assistant Examiner*—Frank Sever
*Attorney, Agent, or Firm*—Richard R. Mybeck

[57] ABSTRACT

A method of decomposing pyrogenic molecules in contaminated water which is disposed within a closed water container to produce, with surprising low energy requirements, pyrogen-free water.

The method comprises placing water which is suspected to contain pyrogenic material (herein called "contaminated") into a sealable pressurizable container, sealing said container, heating said sealed container to a temperature of from about 180° to about 230° C, preferably about 200° C, to create within the container a pressure sufficient, i.e., from about 15 to about 36 atmospheres, to prevent the formation of steam in said container while destroying all pyrogens in the container. After attaining the desired temperature for a brief period, that is, about 1-10 minutes, the heat is removed and the sealed container is cooled to room temperature in any suitable fashion and the water therein is ready for use or storage within the container, as the exigencies of circumstances dictate. When it is desired to use the pyrogen-free water hereby produced for the manufacture of parenteral solutions, the contaminated water will be first deionized using well known techniques such as flowing the water over ion exchange resin to remove the electrolyte therefrom and then subjected to the method of this invention.

9 Claims, 2 Drawing Figures

PREPARATION OF PYROGEN-FREE WATER

DESCRIPTION OF INVENTION

The invention relates to the depyrogenation of water and more particularly to a new and improved method of decomposing pyrogenic molecules in water in a quick, easy and energy conserving fashion.

The invention herein described comprises creating a pressure-temperature relationship within a sealed container of water of suspected contamination in such a manner that the water is maintained in its liquid phase while reaching a temperature sufficient to decompose all of the pyrogenic molecules contained therewithin, that is, a temperature of about 180°–230° C.

More particularly, the method comprises placing contaminated water, that is, water suspected to contain pyrogenic material, into a sealable pressurizable container, sealing said container, and thereafter heating said sealed container to a temperature of from about 180° to about 230° C, preferably about 200° C, whereupon the pressure created within the container, that is, from about 15 to about 36 atmospheres, prevents the formation of steam in said container while destroying all of the pyrogen substance contained therein. After heating for a brief period, the sealed container is cooled to room temperature in any suitable fashion. The water contained therein is then ready for use or storage in its container, as circumstances dictate.

When it is desired to use the pyrogen-free water hereby produced for the manufacture of parenteral solutions, the contaminated water will first be deionized using conventional techniques, e.g., ion exchange, before the water is placed into the sealable pressurizable container.

The adverse effects of some substance (later called "pyrogens") in water was first recognized in about 1923 by Florence B. Seibert who reported her findings at Vol. 67, pages 90–104 of *The American Journal of Physiology* in an article entitled "Fever Producing Substances Found in Some Distilled Waters". Ms. Seibert discovered that the "fever-producing substance" she detected could be destroyed completely by long and drastic heating.

The next significant publication appears to be that of H. M. Banks which appeared at Vol. 4, pages 260–291 of *American Journal of Clinical Pathology* (1934). Banks, as Seibert before him, based his concept for the destruction of the "substance in water causing fever-chill reaction" on a time-temperature relationship and defined a temperature of 140° C for at least thirty minutes as the absolute minimum treatment for effective decomposition.

From these perceptive beginnings, the art has today developed three basic methods for removing pyrogens from water, all of which require exotic materials or the expenditures of vast quantities of energy.

One of the procedures currently used in laboratories needing pyrogen-free water requires special distillation apparatus in which pyrogen-free steam is created, transported to a condenser and there condensed into pyrogen-free water.

Depending upon their capacity, such distillers consume a vast amount of energy. For example, in order to obtain one liter of depyrogenized water in such equipment, approximately 650 K-Cal are needed.

A modified distillation method has been developed which also employs chemical destruction to rid the system of pyrogen molecules. This modified method supplements the thermal effect previously discussed by the addition of potassium permanganate (10 ml 0.1 N per liter) and sodium hydroxide (5 ml 1.0 N per liter) to the contaminated water. This method is also very costly in its high energy requirements and its added raw material expense. It also produces only a very low output; moreover the depyrogenized water is highly ionic and must be distilled again to achieve deionization.

A third prior art method, developed for and restricted to small laboratories, involves placing activated charcoal in the stream of contaminated water to entrain the pyrogen-containing molecules therefrom. While convenient for limited laboratory production, the expense and low capacity of this method renders it totally unsuited for the commercial production of depyrogenated water.

In view of the foregoing, and especially in view of the present keen awareness of the need for energy conservation, an urgent demand exists for a method of depyrogenating water in large volumes with minimal energy requirements.

Accordingly, a prime object of the present invention is to provide a new and improved method of producing pyrogen-free water which substantially reduces the energy requirements of the prior art methods.

Another object of the present invention is to provide a new and improved method of producing pyrogen-free water which avoids the need and expense of introducing special chemical reagents into the contaminated water.

A further object of the present invention is to provide a new and improved method of producing pyrogen-free water which is readily adapted to large scale production.

A still further object of the present invention is to provide a new and improved method of depyrogenating water readily adapted to continuous production of water which is capable of long term storage and deferred use and which can employ reusable containers so as to further reduce unit capital investment.

Still another object of the present invention is to provide a new and improved method of depyrogenating water which is compatible with known procedures for deionizing water and when used in conjunction therewith provides a highly efficient, low cost, low energy dependent method of providing sterile, depyrogenized, and deionized water for the manufacture of parenteral solutions.

These and still further objects, as shall hereinafter appear, are fulfilled by the present invention in a remarkably unexpected fashion as can be readily discerned from a detailed consideration of the accompanying description of certain exemplary embodiments thereof, especially when read in conjunction with the accompanying drawing in which like numbers identify like parts throughout the several views.

Figure 2:
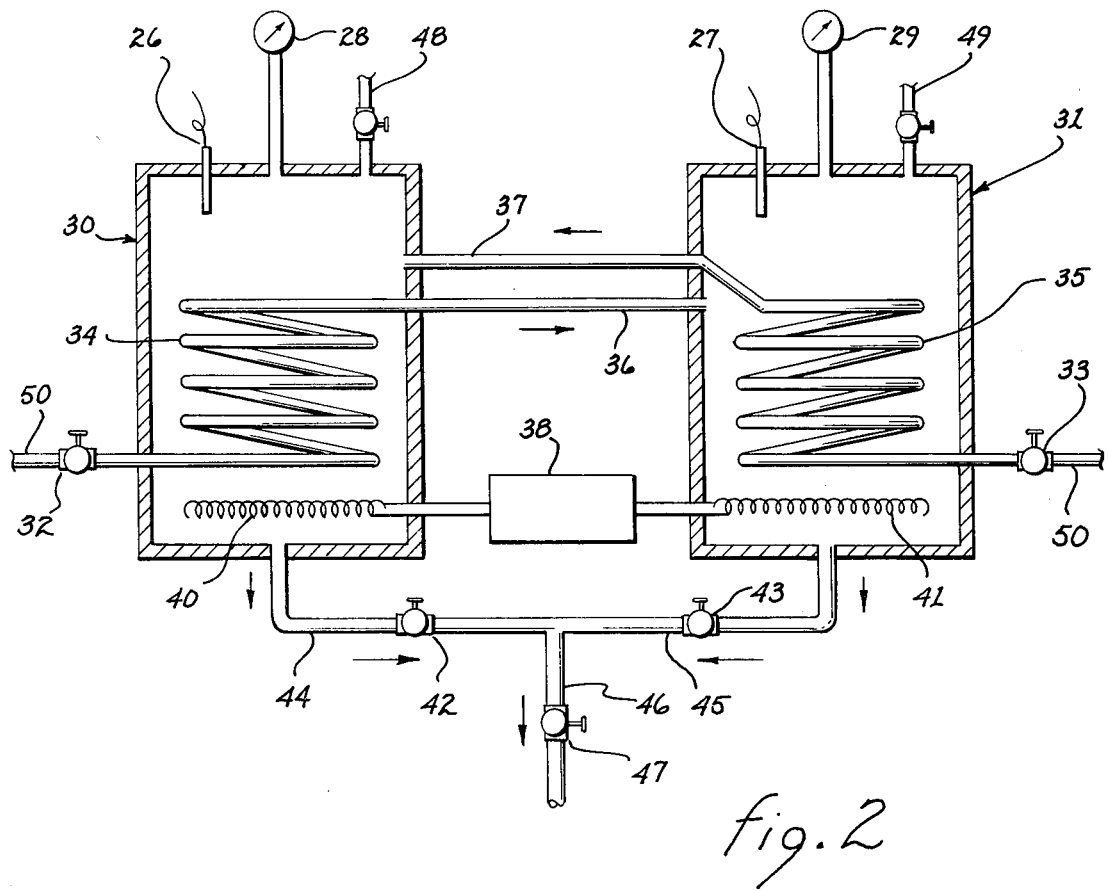

In the drawing:

FIG. 1 is a diagramatic showing of the present invention adapted for low volume laboratory production of depyrogenated water; and FIG. 2 is a diagramatic showing of the present invention adapted for large volume commercial production of depyrogenated water.

In general, practice of the present invention is accomplished by placing the water suspected to contain pyrogenic molecules ("contaminated water") into a pressurizable container, sealing the container, and thereafter heating the sealed container to a temperature of from about 180° to about 230° C, and holding the container at said temperature for a brief period. The sealed container prevents evaporative loss of the liquid as the temperature rises and the ensuing pressure buildup, to 15–36 atmospheres, raises the boiling point of the contents and avoids the enthalpy of steam formation. Thus, a maximum of 200 K-Cal (assuming 0° C starting temperature which is normally not the case) is required to bring each liter of contaminated water up to 200° C (in contrast to the 650 K-Cal per liter required for the distillation process in vogue today). In addition, all pyrogenic substances in the water are decomposed and rendered inert.

"Pressurizable" as used herein with respect to the container/system with which the invention is practiced means that the container/system is constructed to withstand the buildup of internal pressures of at least that required for operational pressures of about 36 atmospheres which limit is obtained by multiplying said 36 by the standard safety factor. A design capable of withstanding internal pressure of at least 150 atmospheres is preferred.

The output obtainable by the present invention is unlimited and the time required to obtain complete destruction of the pyrogen substances is relatively brief (e.g., 1 to 10 minutes, preferably 1 to 5 minutes), especially in contrast to the (30) minute to 24-hour time cycles required by prior art.

Thus, the methodology of the present invention operates at only ⅓ of the energy required by the prior art distillation methods, obtains complete depyrogenation in minimal time, provides depyrogenated water in a condition that it can be stored indefinitely and requires no special controls to maintain the pyrogen-free condition of the depyrogenized water.

As previously explained, when it is desired to use the pyrogen-free water output of the present invention in the manufacture of parenteral fluids, the contaminated water introduced into the method will be deionized first, that is, deionized prior to introduction into the present invention.

Referring now to FIG. 1 of the drawing, a container 10 suitable for laboratory use, that is, having a capacity of one liter, is fabricated from stainless steel, nickel-chrome steel, or the like non-corrodible thermal resistant material. Container 10 comprises a body portion 11 and a lid portion 12.

Body portion 11 comprises a bottom 13 and a mouth 14 interconnected by sides 15. Adjacent mouth 14, and in circumscription therewith an outreaching peripheral flange 16 is formed and functions in a manner to be hereafter described.

Lid portion 12 likewise is provided with a closed end 17 and an open or mouth end 18. An outreaching peripheral flange 19 is formed in circumscription with said mouth 18 and finished to provide, when lid portion 12 is properly seated upon body portion 11, a sealing engagement with flange 16 as bolts 20, 21 are turned to a tightened position.

A suitable manometer 22 and thermometer 23 are each disposed through closed end 17 into operational relationship within container 10 and provide convenient means for monitoring both the temperature and pressure created therewithin when the container 10 is placed in operational relationship to a suitable source of thermal energy, for example, electric heater elements 24. Of course, heating elements 24 can be formed integrally with the container or externally applied either as a conventional hot plate type heater or as a well-type heater or any other of the well known equivalents thereto. As illustrated, container 10 is suitably juxtaposed with a suitable heat source such as electric heat well 25.

In one practice of the present invention using the embodiment shown in FIG. 1, a container 10 is filled with contaminated water, which is first deionized (since it is desired to use the pyrogen-free water output in the manufacture of parenteral solutions), to about 60 percent of capacity and a tightly fitting screw cap is screwed into place to seal the container. The sealed container is then heated to 200° C, producing an internal pressure of 25 atmospheres, and is held at 200° C for one minute. The container is then cooled with cold water which is retained to fill a second container. In cooling the first container, the cooling water is thereby preheated and does not require as much thermal energy to bring it to the desired temperature once the second container is filled and sealed.

The cooled first container thus contains pyrogen-free water which can be stored in the sealed container indefinitely or, if desired, the seal can be broken and the water used immediately.

Referring to FIG. 2, an embodiment of the present invention is illustrated which achieves the continuous production of depyrogenized water. Thus, two or more containers 30, 31 are fabricated in a unitary structure from a suitable non-corrodible thermal resistant material such as stainless steel or the like and are interconnected in a manner to be more fully described. Each container, for example 30, is provided with a fresh water inlet 50 controlled by valve 32 to admit water into and through coils 34 from which the water is passed through conduit 36 into the second container 31. Likewise, inlet valve 33 admits water from inlet 50 into and through coil 35 for passage through conduit 37 into tank 30.

A pressure responsive automatic heating controller 38 is disposed intermediate containers 30, 31 and regulates the heat therein by selectively actuating heating elements 40, 41 respectively in response to the pressure sensors (not shown) associated therewith.

Suitable valves 42, 43, disposed within discharge lines 44, 45, respectively associated with tanks 30, 31, allow depyrogenized water produced therein to be selectively directed into a filling tube 46 which, in turn, is controlled by a suitable valve 47. The actuation of valve 47 allows depyrogenated water to be sterile filled into suitable sealable transport containers (not shown) or the treated water may be pumped directly into other equipment or the like, depending upon the operator's then current need for depyrogenized water. As explained with respect to the batch system, the feed water to be decontaminated is preferably deionized prior to introduction into this system when the purpose for which the sterile water is being prepared is the manufacture of parenteral liquids. The conditions within containers 30, 31 are respectively monitored by thermometers 36, 27 and manometers 28, 29.

In operation, the water to be treated (which, if desired, will be previously deionized) is admitted from water inlet 50 into tanks 30, 31 by opening valves 32, 33. The water, inbound through valve 32, passes through coil 34, conduit 36 into tank 31. Water, inbound through valve 33, passes through coil 35, conduit 37 into tank 30. Thus admitted into the respective tanks 30, 31, the water is heated by elements 40, 41, respectively until the indicated temperature and pressure is obtained whereupon the pyrogenic substances contained within the water is decomposed and rendered inert.

To obtain further energy economy, fresh contaminated water entering the system is preheated in coils 34, 35 as it passes into depyrogenizing reactors 31, 32 respectively.

Obviously, during startup, the preheating cycle herein described will not be functional until the contents of both containers have the opportunity to be heated. Once heated, however, substantial energy economy is realized by preheating the inlet water in the manner indicated.

Heating elements 40, 41 are made of material similar to that used for tanks 30, 31, that is, non-corrosive and thermal resistant, for example, stainless steel.

To further aid in the understanding of the present invention and demonstrate the great utility resulting therefrom, and not by way of limitation, the following examples are presented.

EXAMPLE I

A container, constructed of stainless steel as in FIG. 1, was prepared for laboratory batch production. The container was constructed to withstand pressures of 150 atmospheres. An electric heater was provided with a temperature control. The container was filled to 70% capacity with water known to contain pyrogenic substances, the lid placed on the container and screwed tightly shut to seal the container. The pyrogen substance was obtained from bacteria, standardized, and added to distilled water to prepare a 10 mg/ml concentration. The pyrogen tests were made in accordance with U.S.P. XVI. The heater was then activated and the water in the sealed container was heated to 190° C whereupon the manometer read 21 atmospheres. After one minute at 190° C, the heater was turned off, the container was cooled to room temperature and the cooled container was placed in storage at room temperature for 1 month. After one month's storage, the seal of the container was broken and the water was tested for pyrogen content using the standard U.S.P. test (U.S.P. XVI). The water was found to be 100% pyrogen free.

The batch production was repeated two more times and the results were the same, that is, there was no detectable pyrogen in the water processed according to the present invention.

EXAMPLE II

The batch production experiment of Example I was repeated 3 times at 200° C and 25 atmospheres pressure. Each specimen was held at the indicated temperature for 1 minute and thereafter cooled to room temperature. After storage for one month at room temperature, the seal of each container was broken and the water contained therewithin was assayed for the presence of pyrogenic matter. No pyrogenic matter was detected in any of the samples.

EXAMPLE III

The batch production experiment of Example I was repeated 3 times at 210° C and 30 atmospheres pressure. Each specimen was held at temperature for one minute and thereafter cooled to room temperature. The cooled container was stored for one month at room temperature. Thereafter the seal of each container was broken and the water therein was assayed for pyrogenic matter (U.S.P. XVI). No pyrogenic matter was detected in any sample.

EXAMPLE IV

The batch production experiment to Example I was repeated 3 times at 220° C and 36 atmospheres pressure with the containers filled to 60% of capacity. Each specimen was held at temperature for one minute and thereafter cooled to room temperature. The cooled container was then stored for a month at room temperature. Thereafter the seal was broken on each container and its contents assayed for pyrogenic matter (U.S.P. XVI). No pyrogenic matter was detected in any sample.

EXAMPLE V

A continuous pilot operation was constructed of stainless steel in the manner shown in FIG. 2. Container 30 was filled to 70% of its volume and all valves were closed. The heat control was then activated and the water in container 30 was heated to 180° C at which point the manometer registered 15 atmospheres. Cool water was then introduced through valve 32 into coil 34 wherein it is preheated before passing through conduit 36 into container 31, and the depyrogenized water in container 30 was cooled proportionately. In a similar manner, water entering through valve 33 was preheated in coil 35 before passing through conduit 37 into container 30 to establish a continuous counter-flow procedure. Seven specimens of water, withdrawn from valve 47, were assayed for pyrogenic matter (U.S.P. XVI) and all were found to be pyrogen free.

From the foregoing, it is apparent that a novel method of depyrogenation of water is herein described and illustrated which meets all of the foregoing objectives in a remarkably unexpected manner. It is, of course, understood that such modification, alterations and adaptations as will readily occur to the skilled artisan confronted with this disclosure are intended to be within the spirit of this invention which is limited only by the scope of the claims appended hereto.

Accordingly, what is claimed is:

1. A method for the production of pyrogen-free water having substantially reduced energy requirements comprising: feeding contaminated water into a sealable pressurizable system, said system comprising two containers connected in parallel relative to the feeding of contaminated water thereinto and the removal of pyrogen-free water therefrom and connected serially relative to the flow of the cooling water from one to the input line of the other and the cooling water from the other to the input line of the one; sealing the system; heating the water in said sealed system to a temperature of at least 180° C to about 230° C while maintaining said water substantially entirely in a liquid state; holding said water at said temperature for a period of at least 1 minute; cooling said water in each said container to room temperature with inlet water for the other said container; and removing said cooled pyrogen-free water from said system for use.

2. A method for producing pyrogen-free water while consuming a minimum of energy, comprising the steps of: filling a container with water which contains pyrogens to a volume sufficient to accomodate expansion of said water upon subsequent heating; sealing said volume of water within said container; heating said volume of water to a temperature of at least 180° C while simultaneously controlling the pressure of said volume of said water so as to maintain said water substantially entirely in a liquid state thereby thermally degrading said pyrogens to produce pyrogen-free water without any appreciable vaporization of said water; reducing the pressure and temperature of said volume of said water to ambient pressure and temperature, respectively; and removing said water from said container for use.

3. A method according to claim 2 in which said contaminated water is deionized prior to being fed into said container.

4. A method according to claim 2 in which said contaminated water is preheated prior to being fed into said container.

5. A method according to claim 2 in which said container comprises an individual sealable container in which after said cooling said water can be stored indefinitely before removal therefrom.

6. A method according to claim 5 in which said container is filled to about 80% of its capacity but less than 100% of capacity and thereafter heated to a temperature of at least 180° C and holding said water at said temperature for at least one minute to render all pyrogenic material inert without converting substantially any of said water to steam.

7. A method according to claim 6 in which said container is constructed of a material capable of withstanding pressures of 150 atmospheres.

8. A method according to claim 5 in which the container, when heated, obtains a pressure of from about 15 to about 36 atmospheres therewithin.

9. A system for producing pyrogen-free water comprising:
 first sealable container means for containing a first volume of water,
 second sealable container means for containing a second volume of water,
 first means to feed a first pyrogen-containing water stream to said first container means; said first means comprising first preheater means to indirectly exchange heat between said first stream and said second volume,
 second means to feed a second pyrogen-containing water stream to said second container means, said second means comprising second preheater means to indirectly exchange heat between said second stream and said first volume,
 means to heat said first and second volumes to temperatures of at least 180° C,
 means to maintain said first and second volumes substantially entirely in a liquid state at said temperatures, thereby to thermally degrade pyrogens within said water so as to produce pyrogen-free water therefrom,
 first outlet means to withdraw said pyrogen-free water from said first container means,
 second outlet means to withdraw said pyrogen-free water from said second container means.

* * * * *